United States Patent [19]

Rhiger et al.

[11] Patent Number: 5,402,237

[45] Date of Patent: Mar. 28, 1995

[54] REFLECTION-FREE ELLIPSOMETRY MEASUREMENT APPARATUS AND METHOD FOR SMALL SAMPLE CELLS

[75] Inventors: David R. Rhiger; Gerald A. Garwood, Jr., both of Santa Barbara, Calif.

[73] Assignee: Santa Barbara Research Center, Goleta, Calif.

[21] Appl. No.: 975,304

[22] Filed: Nov. 12, 1992

[51] Int. Cl.⁶ .................................................. G01N 21/01
[52] U.S. Cl. ................................. 356/369; 356/382; 356/244
[58] Field of Search ............... 356/244, 369, 382, 445

[56] References Cited

U.S. PATENT DOCUMENTS

| | | | |
|---|---|---|---|
| 4,565,446 | 1/1986 | Chu | 356/246 |
| 4,582,431 | 4/1986 | Cole | 356/382 |
| 4,795,262 | 1/1989 | Morris | 356/436 |
| 4,927,766 | 5/1990 | Auenbach et al. | 356/445 |
| 5,156,461 | 10/1992 | Moslehi et al. | 250/341 |

OTHER PUBLICATIONS

Spanier, Dr. Richard F, "Ellipsometry, a century old new technique", *Industrial Research*, Sep. 1975, Rudolph Research, 4 pages.

*Primary Examiner*—Richard A. Rosenberger
*Attorney, Agent, or Firm*—W. C. Schubert; W. K. Denson-Low

[57] ABSTRACT

An ellipsometry cell is provided with a transparent lid that is positioned close to a specimen within the cell, thus allowing for a low volume wet chemical treatment of the specimen, and yet prevents interference with the ellipsometry measurements by partial reflections of a probe beam off the outer and inner lid surfaces. This is accomplished by configuring the lid to direct an ellipsometry beam and reflections thereof at different angles, so that the beam but not its reflections enter an ellipsometer analyzer. The lid preferably has an angled outer surface with beam entry and exit windows symmetrically tapering from a central ridge, and its inner surface substantially flat and parallel to the cell base.

16 Claims, 4 Drawing Sheets

REFLECTION-FREE ELLIPSOMETRY MEASUREMENT APPARATUS AND METHOD FOR SMALL SAMPLE CELLS

BACKGROUND OF THE INVENTION

1. Field of the Invention

This invention relates to the ellipsometric analysis of samples enclosed within a small cell, and more particularly to a window structure for the cell that allows accurate ellipsometric measurements to be taken despite the presence of reflections from the window surfaces.

2. Description of the Related Art

Ellipsometry is an established nondestructive optical technique for characterizing the properties of surfaces and surface films, such as film thickness, refractive index, surface oxidation, surface reaction kinetics, catalysis, electrochemistry, corrosion, passivation and anodization. It is described for example in Spanier, "Ellipsometry—A Century Old New Technique", *Industrial Research*, September 1975, pages 73–76. The technique involves directing an elliptically polarized light beam onto the surface of a sample to be analyzed, and detecting the beam reflected from the surface to determine changes in its polarization state; such changes correspond to the properties of the sample surface. Measurements are obtained for tan $\Psi$, the change in the amplitude ratio of the parallel component to the perpendicular component of the light wave upon reflection, and $\Delta$, the change in the phase difference between the parallel component and the perpendicular component of the light wave upon reflection. The quantities $\Psi$ and $\Delta$ are functions of the surface's optical constants, the wavelength of the light used, the angle of incidence, the optical constants of the ambient medium and, for a film covered surface, the thickness and optical constants of the film. $\Psi$ and $\Delta$ are both measured in degrees, and each different combination of these two quantities corresponds to a unique set of surface conditions.

A conventional ellipsometric measurement system is illustrated in simplified form in FIG. 1. A laser 2 generates a beam 4 that is linearly polarized by a polarizer 6, with the linear polarization indicated by polarization vector 8. The beam is typically oriented at about 70° to vertical, and passes through a compensator 10 that converts it to an elliptical polarization, as indicated by the polarization ellipse 12.

The elliptically polarized beam is reflected off the surface of a sample 14, which is assumed in this illustration to be horizontal, and which is shown as having a surface film 16, and is transmitted through an aperture 18 to an analyzer 20. The analyzer is a high quality crystal polarizer that determines the plane of polarization of the reflected linearly polarized light. The process of reflection changes the beam's polarization in accordance with the film thickness and the optical characteristics of the film and sample. To make a measurement, the polarizer 6 is adjusted in such a way that the combined effect of the polarizer, compensator, sample, and film causes the beam entering the analyzer to be linearly polarized, as indicated by linear polarization vector 22. A filter 24 eliminates unwanted background light from the beam transmitted through the analyzer 20 so that measurements can be made in normal room conditions, with the filtered beam sensed by a photodetector 26. The photodetector 26 transmits an electrical signal corresponding to the beam intensity to an extinction meter 28.

There are certain settings of the polarizer that cause the beam reflected from the specimen to be completely linearly polarized. At such settings the analyzer 20 can be rotated to a position at which almost no light reaches the photodetector 26, and the extinction meter 28 moves to its lowest reading. Measurements are taken at two such settings, from which the film thickness, refractive index and other characteristics can be determined with the use of graphs, tables or calculators.

In certain applications it is desirable to obtain ellipsometry measurements within a controlled environment. For such cases several techniques have been used to allow a sample to be analyzed without exposing it to the environment in which the analysis equipment is located; three such arrangements are illustrated in FIGS. 2, 3 and 4. In FIG. 2 a specimen 30 to be analyzed is placed within a sealed chamber 32. Beam entrance and exit ports 34 and 36 into the chamber have respective transparent windows 38 and 40 that allow an analysis beam to be transmitted into and reflected out of the chamber, without impairing the sealed environment within the chamber. Apparatus comparable to that shown in FIG. 1 is used to produce an elliptically polarized entrance beam 42 that is directed through the entrance window 38 onto the specimen 30, and to analyze the exit beam 44 reflected off the specimen. The beams 42 and 44 are generally transmitted at right angles to the surfaces of their respective windows 38 and 40.

In FIG. 3 a sealed chamber 46 is shown with only a single entrance/exit port 48, and a transparent window 50 sealing the port. An elliptically polarized entry beam 52 is transmitted through the window 50 and reflected off the specimen 30 within the chamber. The reflected beam is redirected back onto the specimen by a mirror 54, but at an altered angle so that it reflects off a different portion of the specimen to exit from the chamber as exit beam 56. The entry and exit beams 52 and 56 are offset from each other both spatially and angularly, and the analysis of the exit beam is modified to account for the double reflection off the specimen.

In FIG. 4 another chamber 58 is shown with open entry and exit ports 60 and 62, respectively. This arrangement is similar to that of FIG. 2, except the transparent windows 38 and 40 of FIG. 2 are omitted and a gas inlet port 64 is provided in the chamber 58. An inert gas such as nitrogen (indicated by arrows 66) is admitted into the chamber under pressure through gas port 64 and flows out of both beam ports 60 and 62. This outward flow of inert gas allows ellipsometric analysis to be performed, while effectively sealing the interior of the chamber and the specimen 30 from the outside environment.

A more recent application for ellipsometric measurements concerns monitoring the surface condition of a sample contained within a small volume cell. The purpose of this application is to minimize the volume of wet chemical reagents used in the fabrication of microelectronic circuits. It is illustrated in FIG. 5, and involves the provision of a small volume cell 68 that houses a semiconductor wafer 70, or a portion of a wafer, for chemical processing prior to the fabrication of microelectronic circuitry on the wafer. Such preparation normally involves cleaning, etching, and other wet chemical processing.

The specially designed cell 68 of FIG. 5 substantially reduces the volume of wet chemicals required for the processing, and is the subject of copending patent application Ser. No. 899,792 filed Jun. 19, 1992 by Gerald A. Garwood, Jr., a co-inventor of the present invention now U.S. Pat. No. 5,265,960. U.S. Pat. No. 5,265,960 is assigned to the Santa Barbara Research Center, the assignee of the present application. The wafer 70 is shown supported directly by the cell base 72, although it may alternately be supported off the base by means of standoffs if processing of both faces of the wafer is desired. The cell 68 is covered by a flat transparent lid 74, which is preferably glass but might alternately be formed from a transparent plastic that does not react with the chemicals used in the substrate processing. The lid 74 is fastened to the base 72 by means of bolts 76 around its edge, with an O-ring 78 sandwiched between the lid and base to seal the interior of the cell. The wet chemicals used to treat the wafer are cycled through the cell by means of an inlet port 80 and an outlet port 82 that extend through the base from the exterior of the cell to a location inward of O-ring 78. The clearance between lid 74 and wafer 70 is kept quite small, as is the peripheral spacing between wafer 70 and O-ring 78, thereby greatly reducing the volume of wet chemicals that would otherwise be required to prepare the wafer.

The chemical processing cell 68 is at least theoretically adapted to ellipsometry measurements to monitor the wafer surface at various stages of the processing. In principle, this can be accomplished by directing an elliptically polarized beam 84 at a angle through the lid 74 and onto the upper surface of the wafer 70, with the beam reflecting off the wafer and proceeding back through the lid for analysis; the actual ellipsometry equipment is not shown in FIG. 5, but it would be comparable to that illustrated in FIG. 1. Although the beam 84 is refracted during both passes through the lid 74, these angular deviations cancel each other and the exit beam emerges from the lid at the same angle to vertical as the entry beam (assuming the surfaces of the lid and wafer are parallel). This is important when using the cell 68 in a standard ellipsometry setup, in which the beam entry and exit angles are generally fixed.

A problem in making ellipsometry measurements with the described small volume cell is illustrated in FIG. 6, which shows the elliptically polarized beam 84 incident on the upper surface of the flat transparent lid 74. This incoming beam gives rise to a set of parallel rays that emerge from the cell, due to partial reflections at the upper (outer) and lower (inner) lid surfaces. The primary reflections are an initial reflection of the incoming beam from the lid's upper surface (ray 86), a reflection of the incoming beam from the lid's lower surface, after undergoing refraction at the upper surface/air interface (ray 88), and a double reflection of the outgoing beam from the lid's upper and lower surfaces, after refraction at the lower surface/air interface (ray 90). The outgoing beam itself after reflection from the wafer 70 is indicated by ray 92. Additional parallel rays that emerge from the lid due to multiple reflections are also present, but are of much lower intensity. Because of the small vertical spacing between the lid 74 and wafer 70 to minimize the volume of chemical reagents used, the principal rays 86, 88 and 90 and outgoing beam 92 are grouped close together and two or more of them can enter the analyzer aperture. However, it is only beam 92 that carries the desired information which represents the characteristics of the wafer 70. The other rays carry conflicting and unwanted information that interfere with a proper measurement of the sample within the cell.

The upper and lower lid surfaces could be coated with an antireflection coating to reduce or even eliminate the undesired reflections. However, an antireflection coating would produce further changes in the polarization state of the light passing through it, and the coating on the bottom surface of the lid would be exposed to all the chemical reagents that flow through the cell to treat the wafer. The addition of antireflection coatings is thus not a viable solution. An alternate approach would be to increase the spacing between the reflected rays and the principal ray 92 enough to keep the reflected rays out of the analyzer aperture by substantially increasing the distance between the wafer and the cell lid. This, however, would greatly increase the cell volume and thereby defeat the purpose of having a small cell.

SUMMARY OF THE INVENTION

The present invention seeks to provide an ellipsometry sample cell that effectively segregates reflected rays from the principal beam in the ellipsometry process, and yet is compatible with small volume cells having a narrow spacing between the cell lid and the sample enclosed within the cell.

These goals are achieved with a cell housing that includes entrance and exit windows for the ellipsometry beam that are configured to direct the principal beam and the reflections thereof at different angles, so that the beam but not its reflections enters the ellipsometry analyzer. The windows are preferably implemented in a unitary lid with a flat inner surface, and an outer surface that tapers on each side from a ridge to form flat entrance and exit windows. The outer surfaces of the two windows are preferably flat and at substantially equal angles of about 1°–5° to the lid's inner surface, and are symmetrically arranged on opposite sides of the ridge. The housing is positioned with respect to the beam so that a reflection of the beam off the entrance window's inner surface exits the housing through the outer surface of the same entrance window.

The new lid design facilitates in situ ellipsometry for a small volume cell, thereby providing an objective, operator-independent and reliable means of monitoring the efficacy of cleaning and treating processes applied to the wafer.

Further features and advantages of the invention will be apparent to those skilled in the art from the following detailed description, taken together with the accompanying drawings.

DETAILED DESCRIPTION OF THE INVENTION

Figure 1:
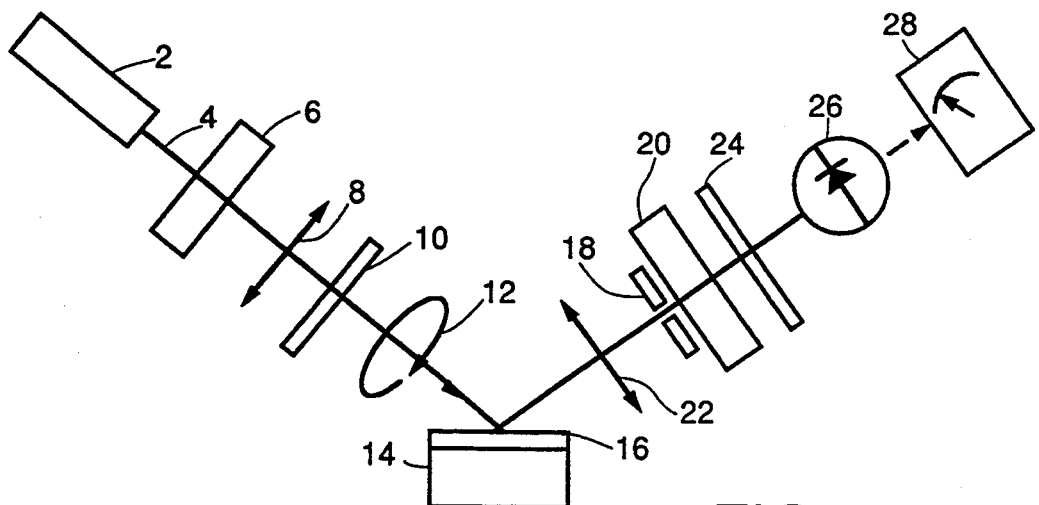
FIG. 1 is a diagram, described above, of a conventional ellipsometry system.
Figure 2:
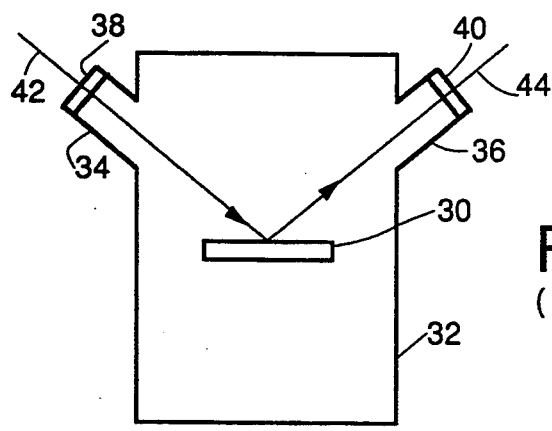
FIGS. 2–4 are simplified elevation views, described above, of prior ellipsometry specimen housings that employ different types of beam windows.
Figure 3:
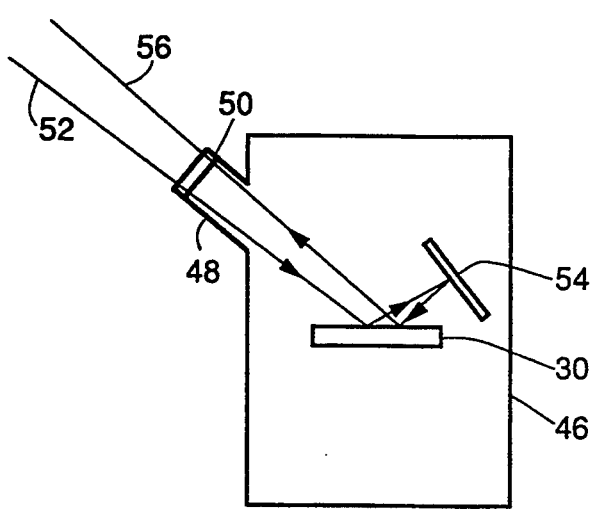
Figure 4:
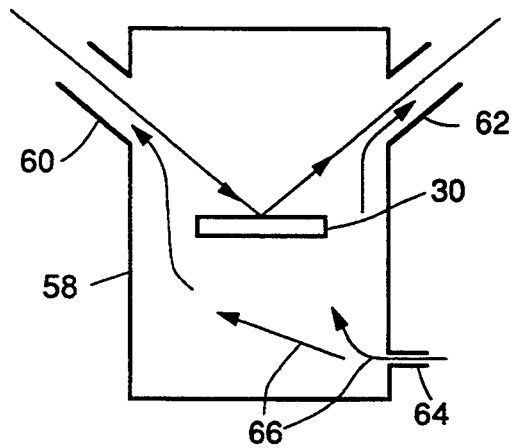
Figure 5:
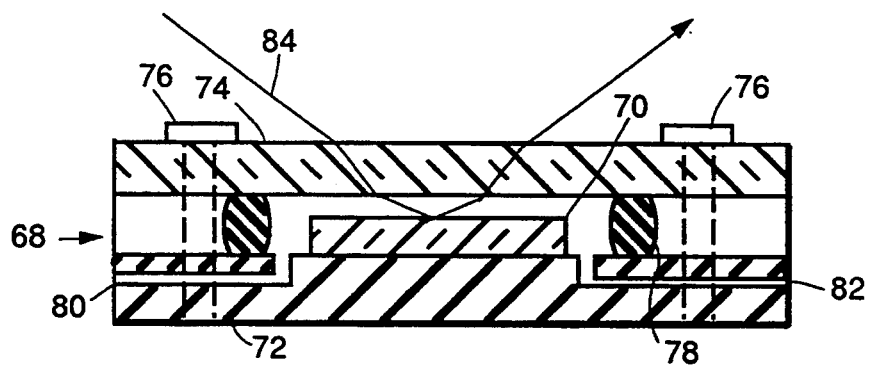
FIG. 5 is a sectional view, described above, of a small volume cell used for cleaning and processing a semiconductor wafer.
Figure 7:
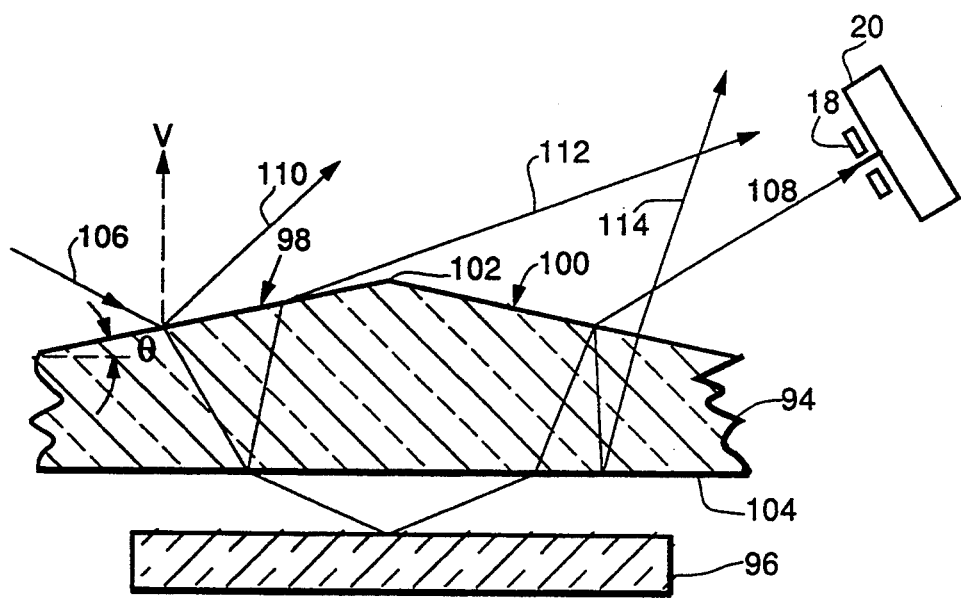
FIG. 7 is a simplified fragmentary sectional view, not to scale, of a new ellipsometry cell lid in accordance with the invention.

The invention provides an ellipsometry cell with a novel lid in which entrance and exit windows are formed at different angles to segregate the principal ellipsometry beam from its reflections at the outer and inner lid surfaces. A preferred embodiment for the lid is shown in FIG. 7, in which only the lid 94, the underlying ellipsometry sample such as semiconductor wafer 96, the ellipsometry analyzer 20 and its associated aperture 18 are illustrated. The lid 94 can be employed in a cell such as that shown in FIG. 5, and can in effect be substituted for the flat lid 74 shown in FIG. 5 and attached to the cell in the same manner. The upper (outer) surface of the lid 94 is divided into an entrance window 98 and an exit window 100, with the two windows meeting at a central ridge 102 from which each window tapers down towards the opposite side of the lid. The entrance and exit windows are preferably flat, although more complicated geometric configurations can be designed that would achieve the optical segregation between the principal and reflected ellipsometry beams obtained by the invention.

The entrance and exit windows 98 and 100 are preferably fashioned at equal angles $\theta$ to horizontal, preferably within the range of about 1°–5°. The larger angles produce a greater dispersion between the principal and reflected beams but also distort the resultant ellipsometry reading to a greater degree; the smaller angles produce a smaller dispersion, but have less of an effect on the ellipsometry reading. As discussed below, the distortion in the ellipsometry reading is due to the refraction of the beam, and can be calibrated out in the final reading.

The inner (bottom) lid surface 104 is preferably flat and parallel to the inner (top) support surface of the cell base 72. This allows for a small interior cell volume, and also causes the ellipsometry beam emerging from the exit window to have the same angle to vertical as the entrance beam; this is important for accommodating the cell to a standard ellipsometer. Conventional grinding and polishing techniques are used to achieve the desired geometry for the lid, which can be formed from the same transparent materials as prior lids.

Figure 6:
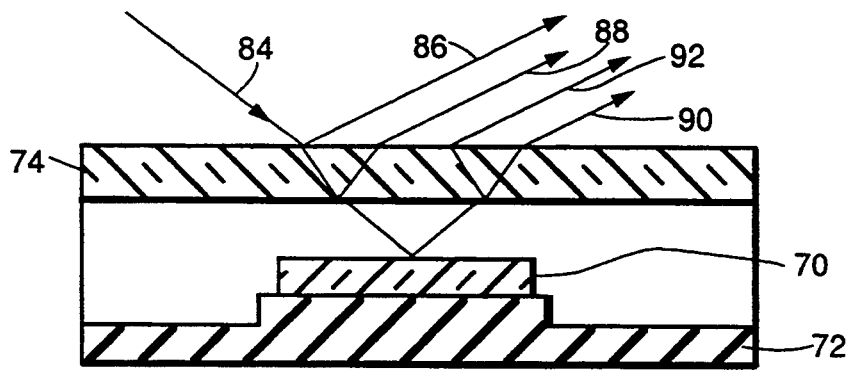
FIG. 6 is a fragmentary sectional view, described above, illustrating the reflection problem encountered by the cell of FIG. 5 during ellipsometry.

Consider an entry ellipsometry beam 106 that is directed onto the outer surface of the entry window. The beam is refracted at the entry window's outer and inner surfaces, reflected off the sample 96 back into the lid, refracted at the exit window's inner and outer surfaces, and emerges as an exit beam 108 that passes through aperture 18 to the analyzer 20. Due to the symmetry of the entrance and exit windows, the exit beam 108 emerges at the same angle to vertical as the entrance beam 106. Partial reflections of the beam from the lid's outer and inner surfaces also occur, in a manner similar to that illustrated in FIG. 6. Specifically, one ray 110 is reflected from the entry window's outer surface, a second ray 112 is reflected from the entry window's inner surface, and a third ray 114 is reflected from the exit window's outer and inner surfaces. The reflected rays 110, 112 and 114, however, are no longer parallel to the principal exit beam 108. Rather, the angled outer lid surface directs them at different angles from the exit beam 108. With an appropriate selection of system dimensions, the reflected rays will diverge sufficiently from the exit beam 108 to ensure that they do not pass through the analyzer aperture 18.

For a specific example, assume that the entry and exit beams 106 and 108 are both at a 70° angle to vertical (a vertical axis is labeled V in the figure), that the refractive index of the lid material is 1.55 (corresponding to glass), and that the pitch angle of the outer surfaces for the entry and exit windows is 1° to horizontal. With these assumptions, ray 110 will emerge at an angle of 68.0° to vertical, ray 112 at an angle of 76.475° and ray 114 at an angle of 63.851°.

The principal exit beam 108 thus emerges at the desired angle of 70°, while the reflected rays are diverted away from it. Given a typical spacing of 90 mm from the sample location to the analyzer aperture 18, the smallest angular difference between the exit beam 108 and any of the reflection rays (70.0°−68.0°=2.0°) leads to a minimum displacement between the principal beam and the reflection rays of 3.1 mm at the aperture location; this is larger than the typical aperture diameter of 1.8 mm, and is also larger than the typical beam diameter of 1 mm. The net result is to permit ellipsometry measurements to be performed on a sample that is contained within the desired small volume cell without interference from the reflections.

Figure 8:
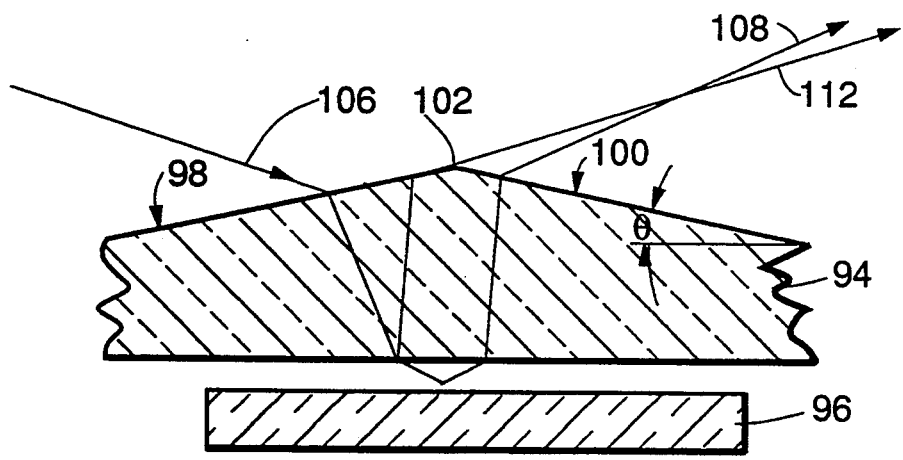
FIG. 8 is a fragmentary sectional view of the new cell lid provided by the invention, with a more accurate scaling than FIG. 7.

It is necessary to align the entry beam 106 fairly carefully with respect to the cell so that the ray 112 reflected from the inner surface of the entry window emerges from the lid on the entry window side of ridge 102, while the principal exit beam 108 emerges on the exit window side of the ridge; if they both emerge through the same window they will be parallel. FIG. 8 is a modification of FIG. 7 that more accurately illustrates the dimensions involved for a small cell application, and demonstrates the need for careful alignment. The close spacing between the lid 94 and the semiconductor wafer 96 results in a proximity of reflected ray 112 to the principal exit beam 108. It is desirable that the ridge 102 separating the entrance and exit windows be well defined and not overly rounded, to maintain the segregation of reflected ray 112 from exit beam 108. For a beam diameter of 1 mm and $\theta = 1°$, the minimum gap between the inner surface of the lid and the upper substrate surface to ensure that the ray 112 and exit beam 108 are fully on opposite sides of the ridge is 0.31 mm; for $\theta = 2°$ the minimum gap size is 0.25 mm.

Figure 9:
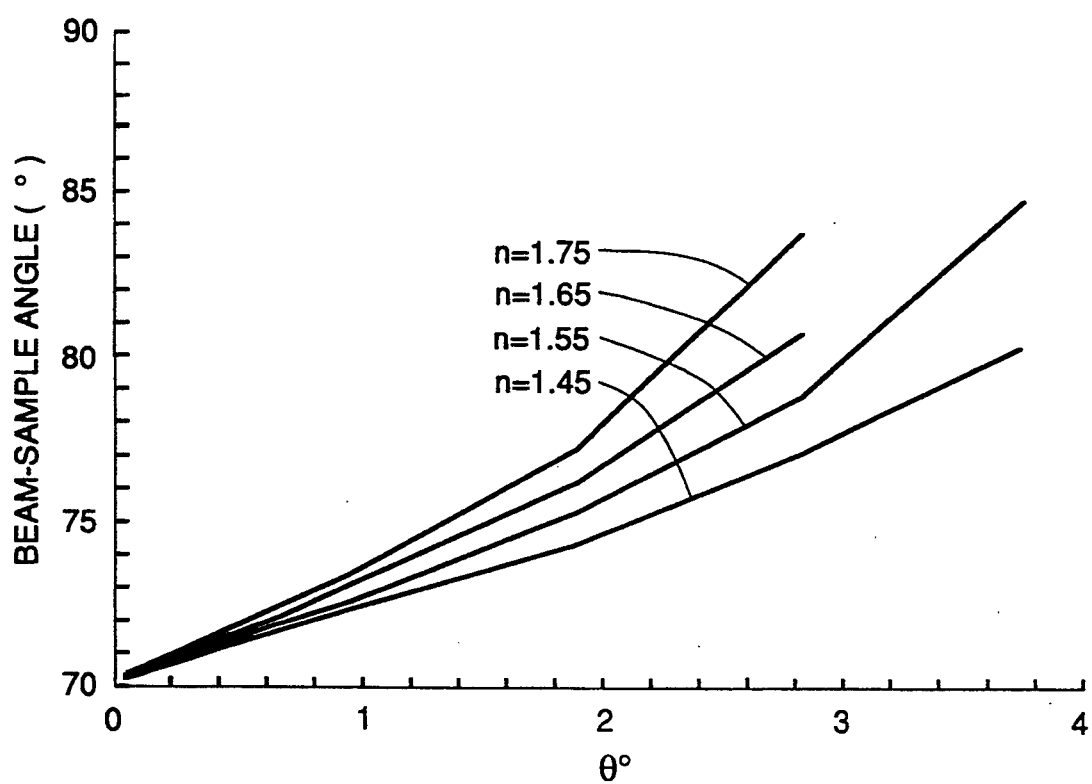
FIG. 9 is a graph plotting the light beam exit angle from the new lid as a function of the lid's upper surface angle and refractive index, from which a calibrated correction for measurements obtained with the invention may be made.

The angle of the lid's outer surface changes the angle at which the principal beam 106 strikes the sample surface, and this in turn alters the sample's effect upon the beam polarization. While a greater angle $\theta$ will reduce the precision required in the positioning of the beam relative to the lid, it will increase the angular deviation at which the beam strikes the sample and will thus produce a greater change in the ellipsometer reading. This effect is illustrated in FIG. 9, in which the angle (to vertical) at which the entry beam strikes the sample is plotted against $\theta$ for different values of refractive index n. This alteration in the ellipsometry values can be compensated by taking measurements on known samples both inside and outside the cell to produce a calibration chart between the two sets of measurements. When measurements are later taken for an unknown sample within the cell, the calibration chart can be used to adjust the measured results by eliminating the effects of the change in beam angle induced by the angled lid.

In a similar fashion, transmitting the beam through the lid will itself introduce modest changes in the ellipsometry parameter values, irrespective of any changes in the angle at which the beam strikes the sample. Again, a calibration chart can be established by taking measurements on known samples using a lid with parallel inner and outer faces, with a thick lid and a large spacing between the lid and the sample to separate the emerging rays.

The lid's thickness will generally be on the order of about 4 mm. It could theoretically be made thinner, but this could impair the strength and rigidity required for screwing the lid to the base around its edge. Thicker lids may be required for larger cells, which are typically about 4–8 cm wide.

While a particular embodiment of the invention has been shown and described, numerous variations and alternate embodiments will occur to those skilled in the art. For example, the outer lid surface might be provided with a rounded dome shape rather than a sharp ridge to separate the entrance and exit windows, although this would increase the precision required in positioning the lid relative to the ellipsometry beam, and could result in the exit beam having an angle different from the entry beam. Accordingly, it is intended that the invention be limited only in terms of the appended claims.

We claim:

1. In an ellipsometry system having means for holding a sample to be ellipsemetrically analyzed, means for directing an elliptically polarized beam onto said sample, and means for analyzing the beam reflected from the sample, the improvement comprising the provision of said sample holding means as:
   a housing for enclosing said sample, and
   a unitary lid for said housing having entrance and exit windows that are substantially transparent to and partially reflect said beam, said windows being oriented at different respective angles to said beam and being configured to direct said beam and window reflections at different angles so that said beam but not said window reflections enter said analyzing means.

2. The ellipsometry system of claim 1, wherein the inner surface of said lid is substantially flat and the outer surface tapers on each side from a ridge, the opposite sides of said ridge comprising said entrance and exit windows, respectively.

3. The ellipsometry system of claim 2, wherein the inner surface of said lid is disposed at substantially equal angles to the axes of said beam directing means and of said analyzing means, and its outer surface on each side of said ridge is substantially flat.

4. The ellipsometry system of claim 2, wherein the outer surfaces of said entrance and exit windows are disposed at substantially equal angles to the lid's inner surface.

5. The ellipsometry system of claim 4, wherein said entrance and exit windows are substantially symmetrical on opposite sides of said ridge.

6. The ellipsometry system of claim 2, wherein the outer surfaces of said entrance and exit windows are each disposed at an angle within the approximate range of 1°–5° to the lid's inner surface.

7. The ellipsometry system of claim 2, wherein said housing is positioned with respect to said beam directing means so that a reflection of said beam off the inner surface of said entrance window exits the housing through the outer surface of said entrance window.

8. A cell for holding a sample for ellipsometric analysis, comprising:
   a base,
   means for supporting a sample with respect to said base,
   a substantially transparent lid having inner and outer surfaces, wherein the outer lid surface comprises a plurality of sections that are oriented at different respective angles relative to the base, and
   means for holding said lid in sealed relation to said base,
   said lid being configured so that, in response to an ellipsometric analysis beam being transmitted through the lid and reflected off a sample within the cell back out through the lid, primary reflections of the beam from the lid's upper and lower surfaces and directed out of the cell at different angles from the analysis beam.

9. The sample cell of claim 8, wherein the outer lid surface comprises a pair of substantially flat sections that taper from each side of a ridge.

10. The sample cell of claim 9, wherein the inner lid surface is substantially flat.

11. The sample cell of claim 10, wherein said outer lid surface sections are disposed at substantially equal angles to the lid's inner surface.

12. The sample cell of claim 10, wherein said outer lid surface sections are each disposed at an angle within the approximate range of 1°–5° to the lid's inner surface.

13. A method of ellipsometrically analyzing a sample, comprising:
   directing an elliptically polarized beam onto said sample through a substantially transparent entrance window, and reflecting said beam off said sample and through a substantially transparent exit window, wherein said entrance and exit windows are provided with a flat common surface facing said sample, and respective outer surfaces facing away from said sample at different angles,
   directing surface reflections of said beam from said entrance and exit windows at different angles to said reflected beam to segregate them from the reflected beams, and
   positioning an ellipsometric analyzer to detect and analyze said reflected beam but not said surface reflections.

14. The method of claim 13, further comprising the steps of chemically processing said sample prior to said ellipsometric analysis, and then performing said ellipsometric analysis in situ.

15. The method of claim 13, said entrance window refracting said beam to alter the angle at which said beam strikes the sample, further comprising the step of calibrating said ellipsometric analysis to compensate for said altered angle.

16. The method of claim 13, further comprising the step of calibrating said ellipsometric analysis to compensate for changes in ellipsometry readings resulting from the transmission of said beam through said entrance and exit windows.

* * * * *